United States Patent [19]

Kadish

[11] Patent Number: 4,722,896

[45] Date of Patent: Feb. 2, 1988

[54] METHOD FOR AFFINITY PURIFICATION OF HYBRIDOMA ANTIBODIES

[75] Inventor: Julian L. Kadish, Norton, Mass.

[73] Assignee: The Beth Israel Hospital Association, Boston, Mass.

[21] Appl. No.: 276,189

[22] Filed: Jun. 22, 1981

Related U.S. Application Data

[63] Continuation-in-part of Ser. No. 228,548, Jan. 26, 1981, abandoned.

[51] Int. Cl.[4] ...................... C12P 21/00; C12N 15/00; C12N 5/00
[52] U.S. Cl. ................................... 435/68; 435/172.2; 435/240; 935/108; 530/413; 436/548
[58] Field of Search ................. 435/172, 240, 241, 68; 424/85, 88; 260/112 R; 436/548

[56] References Cited

U.S. PATENT DOCUMENTS

| | | |
|---|---|---|
| 3,645,852 | 2/1972 | Axen et al. |
| 3,995,018 | 11/1976 | Sjöquist |
| 4,081,244 | 3/1978 | Polito et al. ........................ 23/230 B |
| 4,350,683 | 9/1982 | Galfre et al. ........................... 435/68 |
| 4,427,653 | 1/1984 | Springer ............................... 435/948 |

OTHER PUBLICATIONS

Hurn et al., "Production of Reagent Antibodies" Methods in Enzymology vol. 70, (1980) pp. 127-130.
March et al., "A Simplified Method for Cyanogen Bromide Activation, Agarose for Affinity Chromatography." Analytical Biochemistry 60 (1974) pp. 149-152.
Litman et al., "Rapid Purification of IgA from Human Serum" Biochemica et Biophysica Acta, 263 (1972) pp. 89-93.
Yelton et al, "Monoclonal Antibodies" American Scientist 68 (1980) pp. 510-516.
Yeung et al, "Purification of an Ammonium-Inducible Glutamate Dehydrogenase and the use of its Antigen Affinity Column-Purified Antibody in Specific Immunoprecipitation and Immunoadsorptio Analytical Biochemistry 110 (1981) pp. 216-228.
Pel-Freez Biologicals 1983 Catalog, P.O. Box 68, Rogers, AR 72756 pp. A4, B2 and B4.
"Antibody Reagents Revolutionizing Immunology", Jeffrey L. Fox. C&EN, Jan. 1, 1979, pp. 15-17.
"Monoclonal Antibodies" Cesar Milstein, pp. 66-74.
"Monoclonal Antibodies", Dale E. Yelton et al., *American Scientist*, vol. 68, 1980, Sept.-Oct., pp. 510-516.

*Primary Examiner*—J. E. Tarcza
*Attorney, Agent, or Firm*—Lorusso & Loud

[57] ABSTRACT

An efficient process design for purifying large quantities of specific antibodies by affinity chromatography is disclosed. By utilizing the process strategy described, large scale production of highly purified hybridoma antibodies and other proteins becomes feasible.

The initiation of the process centers on production of hybridoma proteins which bind to a commonly available inexpensive protein such as human serum albumin (HSA) with which large quantities of a protein such as mouse immunoglobulin can be isolated by affinity chromatography. The mouse immunoglobulin is covalently linked to an inert matrix, such as Sepharose beads and this affinity reagent is used to purify a large quantity of a hydridoma protein such as rat anti-mouse IgG antibody. This rat anti-mouse IgG antibody can then be linked to Sepharose beads and can be used as a general affinity reagent for the purification of any mouse immunoglobulin.

16 Claims, 1 Drawing Figure

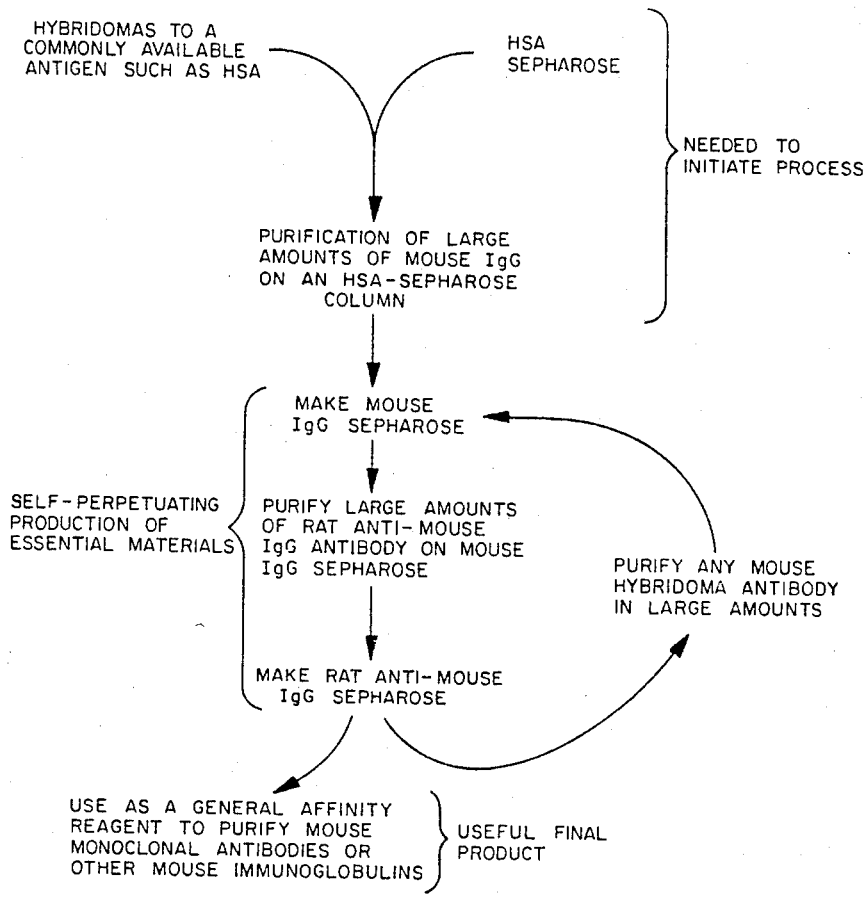

METHOD FOR AFFINITY PURIFICATION OF HYBRIDOMA ANTIBODIES

CROSS REFERENCE TO A RELATED APPLICATION

This application is a continuation-in-part of U.S. application Ser. No. 228,548 entitled "Growth Medium and Process for Producing Monoclonal Antibodies", filed Jan. 26, 1981 now abandoned, the teachings of which are incorporated herein by reference.

BACKGROUND OF THE INVENTION

This invention relates generally to the production of hybridoma proteins and more specifically to the production of hybridoma antibodies.

It has been postulated that if one could isolate one cell making a single specific antibody and grow it in culture, the cell's progeny or clone would be a source of large amounts of identical antibody against a single antigenic determinant-a monoclonal antibody. Unfortunately, antibody-secreting cells cannot be maintained in a culture medium.

There are malignant tumors of the immune system called myelomas, however, whose rapidly proliferating cells can produce large amounts of abnormal immunoglobulins called myeloma proteins in a culture medium. In more basic terms, a myeloma is an old tumor which is no longer capable of producing antibodies (a plasmocytoma). In 1975, investigators learned how to fuse mouse myeloma cells with lymphocytes from the spleen of mice immunized with a particular antigen. The resulting hybrid-myeloma, or "hybridoma", cells express both the lymphocyte's property of specific-antibody production and the immortal character of the myeloma cells.

By following the fusing or splicing technique discussed above which is described in articles entitled "Antibody Reagents Revolutionizing Immunology" by Jeffrey L. Fox, Jan. 1, 1979, C & EN, and "Monoclonal Antibodies" by Yelton and Scharff, *American Scientist*, Vol. 168, pp. 510–516, cells that secrete antibodies can be made immortal by fusing them with tumor cells and cloning the hybrids. Each clone is a long-term source of substantial quantities of a single highly specific antibody. Highly specific monoclonal antibodies produced by this general method have proved to be a remarkably versatile tool in many areas of biological research and clinical medicine. It is these hybridomas which produce antibodies or "hybridoma antibodies" as they can be called toward which the present invention is directed.

Once an antibody producing clone is produced from a hybridoma, cloned cells can be utilized to produce antibodies in two ways. One method is to inject the cloned cells into the belly of a mouse. While in the belly of the mouse, the antibody producing clone proliferates and the antibody it makes becomes concentrated by the mouse in the fluid of the belly (ascitic fluid) and in the blood. The antibody is harvested by tapping the fluid from the belly atraumatically with a needle and syringe. A major disadvantage, however, of raising the hybridoma antibody in vivo is that in the process, the hybridoma product becomes mixed with all of the other immunoglobulins present in the mouse and is no longer monoclonal.

Of course the alternative to any in vivo procedure like the one discussed above is an in vitro procedure. The problem with producing antibodies from hybridoma in culture, however, results from the fact that the hybridoma releases the antibody in the culture medium to produce a very dilute antibody containing liquid. Indeed the amount of antibody in a tissue culture supernatant is typically in the order of about 10 micrograms per milliliter. As can be appreciated, recovery of an antibody from such dilute supernatant greatly increases recovery costs.

However, an in vitro procedure has at least one distinct advantage over an in vivo procedure. The marked advantage of the in vitro procedure is that the culture conditions can be easily arranged so that the species of immunoglobulin being produced in the culture (the hybridoma product) is different from that of any other which may be contaminating the culture medium. For example, bovine serum normally has to be added to the culture system and thus bovine immunoglobulins will be mixed with the hybridoma product (normally mouse or rat).

The important point is that in an in vitro production method, conditions can be easily adjusted so that the hybridoma product being grown is unique with regard to its derivative species and that is not the case with the fluid recovered from the belly of an animal.

The major problem to be dealt with, in raising hybridoma antibodies or other proteins in vitro is to devise a method of purifying and concentrating the desired monoclonal antibody without co-purifying the chemically similar immunoglobins derived from the serum supplement to the tissue culture medium. Of course it would be highly desirable to have a reagent which is specific for the protein to be recovered (mouse immunoglobulin for example).

In short, hybridoma antibodies and other proteins produced in tissue culture occur at very low concentration and thus are difficult to purify in good yield at reasonable cost. On the other hand, proteins such as antibodies produced in vivo are contained in a fluid with other proteins which present purification problems. Both problems would be reduced if one had available large quantities of a reagent that binds mouse immunoglobulins or other proteins specifically.

SUMMARY OF THE INVENTION

In accordance with the present invention, one hybridoma antibody is produced and collected against an inexpensive protein such as human serum albumin. Human serum albumin is relatively inexpensive and is used to initiate a process which produces a reagent for collecting the protein to be recovered. With a column loaded with such a reagent, a means exist for the continued recovery of antibodies and other proteins from dilute solutions.

Accordingly one important object of the invention is to provide a method for the economical recovery of proteins including antibodies from dilute solutions.

BRIEF DESCRIPTION OF THE DRAWING

The sole FIGURE of the drawing is a flow sheet of the process in accordance with the present invention.

DESCRIPTION OF THE PREFERRED EMBODIMENTS

At the outset the invention is described in its broadest overall aspects with a more detailed description following. In its broadest overall aspects the protocol of the present method employs one hybridoma protein, for example a rat anti-mouse immunoglobulin hybridoma antibody, to bind the protein to be recovered, for example a mouse antibody. As is readily apparent to those skilled in this art, anti-mouse immunoglobulin is an antibody that reacts with mouse immunoglobulin or antibody. A rat is selected to produce the anti-mouse immunoglobulin because of the good fusion efficiency that is obtained by fusing the spleen cells from a rat with the mouse myeloma. Of course any animal could be utilized which enables the production of hybridoma producing proteins specific to the protein to be recovered. An important aspect of the present process is to make a large amount of the protein such as the rat antimouse IgG which is specific to the product to be recovered.

However, in order to make such an affinity reagent, a source of mouse IgG (or other specific protein) is needed so that sufficient quantities of rat antimouse IgG may be easily purified. Unfortunately large amounts of mouse IgG can't be made from a mouse because a mouse has too little to begin with.

However, it is possible to make another hybridoma which produces protein specific against a protein or antigen which is easily available in large quantities. Such an antigen is human serum albumin (HSA).

Thus in accordance with the present invention, the preferred inexpensive starting material is HSA. The HSA is immobilized on an affinity matrix such as Sepharase beads (product of Pharmacia).

A next step, for example, is to make a mouse anti-HSA hybridoma (to be used as the source of mouse IgG) and purify the antibody produced on an HSA affinity column. Such a column will collect a large quantity of mouse IgG. The mouse IgG is then separated from the HSA column and used to prepare a mouse IgG column. The mouse IgG is then linked to an affinity chromotography column to produce a mouse IgG column.

The next step in the procedure is to produce a rat anti-mouse hybridoma.

Next the rat anti-mouse antibody is collected on the mouse IgG column. The rat anti-mouse immunoglobulin is then separated by acid elution and used to make a rat anti-mouse immunoglobulin column which is a general reagent for the extraction and purification of mouse antibody from culture supernatant.

It should be noted that the mouse IgG directed against the commonly available antigen, HSA, is needed only to initiate this general purification scheme. For example, once one obtains one gram of mouse anti-HSA, when linked to the Sepharose matrix, that one gram can be used to make two grams of rat anti-mouse IgG antibody. This, in turn can be used to purify four grams of mouse IgG directed against any antigen. This additional mouse IgG, when linked to the Sepharose matrix, can in turn be used to make eight grams of rat anti-mouse IgG. Thus, this system can be both self perpetuating as well as providing, a purification method for obtaining any protein (hybridoma or otherwise) in pure form. It should be noted that this same method can be used to make large quantities of any affinity reagent such as mouse anti-rat IgG or mouse anti-human IgG. It should also be noted that, in general this same method can be applied to hybridoma products raised in the ascitic fluid form but in that case the purified products obtained are no longer strictly monoclonal.

The invention is further illustrated by the following nonlimiting example in which:

Balb/C is a particular inbred strain of mouse
CFA is complete Freund's adjuvant
IFA is incomplete Freund's adjuvant
SC is subcutaneously
IV is intravenous
PEG is polyethylene glycol 1000
BSA is bovine serum albumin
RT is room temperature (20° C.)
DMEM is a standard tissue culture medium commercially available from Grand Island Biological Co., Grand Island, N.Y.
$DMEM_A$ is DMEM supplemented with antibiotics
$DMEM_{10A}$ is DMEM supplemented to 10% with calf serum and antibiotics
HAT is DMEM and serum with hypoxanthine, aminopterin, and thymidine.
HT is HAT without aminopterin.
PBS is phosphate buffered saline which is 0.15M NaCl, 0.01M phosphate at pH 7.3
Tris is Tris(hydroxymethyl)aminomethane buffer, product of Sigma Chemical Co.
DMSO is dimethyl sulfoxide
$PO_4$ is total phosphate ion
CS is calf serum
$\bar{c}$ means "with" and $\bar{o}$ means "without".

GENERAL PROCEDURE USED

Hybridoma Summary

The specific plasmacytoma used for fusion with the spleen cells in this procedure was the non-secreting variant of MOPC 21 which is designated P3-NSI-1-Ag4-1.

Balb/C mice or Lewis rats were immunized according to the following schedule.

Immunize $\bar{c}$ antigen-in CFA, 20–50 μg injected SC in 2 sites
  | (14–30 days)
Boost $\bar{c}$ 20–50 μg in IFA, SC in 2 sites
  | (14–30 days)
Inject $\bar{c}$ 20 μg IV
  | 4 days
Remove spleen $\bar{c}$ sterile technique Make single-cell suspension
Mix 10:1 (spleen:myeloma) ratio of cells
Add 32% PEG for total of 8 minutes, including 3 minute spin (1200 RPM)
Remove PEG, add medium
Incubate at 37° C. for 24 hours in bacteriological plate
The cells are washed, resuspended in selective medium (HAT), and then plated in 96 well tissue culture plates. The HAT medium is changed about every other day.

At about day 10, the medium is changed to HT, the wells are tested for antibody activity, and positive wells are subcloned. In successful lymphocyte-myeloma fusions, spleen cells transfer mechanism to survive in aminopterin.

Radioimmunoassay Procedure (Used to test for antibody activity)

1. Add in 25λ the antigen (40 μg/ml) to wells of a 96 well polyvinyl chloride plate.
2. Cover plate $\bar{c}$ Parafilm. Incubate at 37° C. for 1–2 hours. Plates can then be refrigerated $\bar{o}$ removing excess fluid from wells for several days.

3. Aspirate fluid from wells without touching sides of wells. Wash 4–5 times c̄ PBS (containing 1% BSA, 0.02% NaN₃). Fill wells and incubate at RT, uncovered for ½ hr.

4. Aspirate fluid from wells without touching the plastic. Add 25λ of antibody sample to designated wells. Cover c̄ parafilm and incubate 20–24 hours at RT.

5. Aspirate fluid and wash 4–5 times c̄ PBS (containing 1% BSA, 0.02% NaN₃). Add 25λ $I^{125}$ goat antimouse IgG (or goat antirat Ig if a rat hybridoma is being tested for). Cover c̄ parafilm and incubate in hood, behind lead shield for 20–24 hours at RT.

6. Aspirate fluid and wash 4–5 times c̄ PBS (containing 1% BSA, 0.02% NaN₃). Let wells dry.

7. Cut out wells into individual tubes.

8. Count in gamma spectrometer.

CELL FUSION

Preparation of Spleen Cell Suspension (Everything at Room Temp.)

Kill mouse by cervical dislocation. Swab left side of mouse c̄ alcohol (scrub solution). Place mouse on sterile pad. Using sterile instruments (scissors, forceps), cut through skin and pull back. Cut through abdominal wall and remove spleen. Place spleen in sterile petri dish containing sterile PBS. Bring dish to tissue culture hood. Rinse with PBS and remove excess. Add small amount of $DMEM_4$. Tease spleen apart using scalpel and forceps (c̄ teeth). Draw suspension gently up and down syringe several times. Transfer suspension to sterile tube and allow clumps to settle. Transfer suspension without clumps to a second tube containing ~10 ml $DMEM_4$. Centrifuge cells, 800 rpm 5 minutes. Remove supernatant. Resuspend pellet in 1 ml lysing solution (9 parts 0.83% NH₄Cl, 1 part 0.17M Tris pH 7.65). Let solution sit 5 minutes. Add 10 ml $DMEM_4$ and spin again. Resuspend pellet in ~15 ml $DMEM_4$. Count spleen cells in hemocytometer.

CELL FUSION

Day 0

Melt stock PEG at 37° C. Dilute an aliquot PEG to 32% c̄ $DMEM_4$. Count MOPC tumor cells (it may be necessary to spin down if volume is too large). To a round-bottomed Falcon tube, add a ratio of 4:1–10:1 (spleen to MOPC) cells. Spin cell mixture down at 800 rpm for 5 minutes. Suction off supernatant. Resuspend pellet by tapping tube sharply. Add 0.5 ml 32% PEG to pellet, shake very gently (briefly). Allow mixture to set 3 minutes, then spin mixture at 1200 rpm, 5 minutes. Suction off supernatant. Gently resuspend pellet in 1 ml $DMEM_4$. Add the 1 ml of $DMEM_4$ containing the cells to ~10 ml $DMEM_{104}$ in bacteriological plate. Incubate overnight at 37° C.

Day 1

Spin down cells 800 rpm, 5 minutes. Resuspend pellet in 40 cc HAT medium. Aliquot 200λ/well for two 96-well tissue culture plates (flat-bottomed).

Day 2

Change medium of two plates (suck out half medium and add fresh HAT). Change HAT every other day (approximately). At about day 9 or 10, test visible clones for activity (you can wait longer if clones are small). At day 10 change medium to HT. When positive wells have become heavy, transfer them to cloning plates. Keep changing HT on original plates until all positive clones have been transferred to cloning plates.

Procedure for Cloning

Take contents of one well (positive) and resuspend in 1 ml of HT medium in a polypropylene tube. Using a sterile tip, take 100λ from the 1 ml and fill two chambers of a hemacytometer. Count cells-retain uncloned stock in culture as a reserve. Make a stock solution of 5000 cells/ml. Make four dilutions of cells: 50 cells/ml (10 cells/well in 200λ); 25 cells/ml (5 cells/well); 5 cells/ml (1 cell/well); 2.5 cells/ml (0.5 cell/well). Pour dilutions into small petri dishes. Aliquot 200λ/well, 2 rows/dilution. Change medium ~ once/week. When clones appear, test wells for activity. When positive wells have heavy growth, transfer contents of well to 0.5 cc HT medium is one well of 24 well plate. When growth heavy in 24 well plate transfer contents to 4 cc medium in T25 tissue culture flask. Cells can be frozen or expanded.

Procedure for Freezing Cells

Starting c̄ ~5 cc cells suspended in medium they've conditioned, add 0.45 cc sterile DMSO. Using pipette, mix DMSO c̄ cell suspension. Quickly transfer cells to freezing tubes (about 1 ml/tube). Transfer freezing tubes to a −80° C. freezer to permit slow freezing. Then transfer frozen tube to a cane and then immediately into a liquid nitrogen freezer for long term storage. Some hybridoma lines have a tendency to stick to plates and may have to be trypsinized prior to freezing.

Procedure for Thawing Cells

Remove designated tube from cane. Immediately place it in 37° H₂O. As soon as cells are thawed, take contents of tube and add to 10 cc $DMEM_{104}$. Spin down cells 800 rpm, 5 minutes. Resuspend pellet in $DMEM_{104}$ for culture.

Procedure for Trypsinizing Cells (if necessary)

Remove medium. Add sterile PBS ō Ca⁺⁺, Mg⁺⁺. Remove PBS. Add trypsin solution (0.5 cc/T25, 1.5 cc/T75, 3 cc/T150). Let flask sit until cells come off bottom of flask (5–15 mins.). Add medium to flask and transfer contents to a sterile tube. Spin down 800 rpm, 5 minutes. Resuspend pellet in medium.

Procedure for covalently linking proteins in Sepharose beads (method March et al., Analyt. Bioch., 60: 149–152, 1974)

1. Using a scintered glass funnel and vacuum flask attached to a vacuum line, wash approximately 150 ml of Sepharose 4B CL with 5 liters of water to remove all traces of sodium azide.

2. Transfer the Sepharose to a 1 liter beaker and make a slurry 1 part Sepharose: 2 parts 2M Na₂CO₃.

3. Place the slurry in an ice bath on a magnetic stirrer in a hood. Stir until slurry is 7° C.

4. Add 1 ml of CNBr solution/10 ml Sepharose. Watch for precipitation of CNBr. Stir vigorously (or shake by hand) for 1–2 min after CNBr has gone back into solution. Drop pipet and all material that has CNBr on it into a large beaker containing several grams of NaOH pellets. Allow all material to sit for 24 hrs under the hood before discarding or cleaning. CNBr solution: 2 g CNBr/ml acetonitrile. Store frozen.

5. Pour the slurry into a scintered glass funnel attached to a vacuum flask. Wash with:

1.2 1 0.1M NaHCO₃ pH 9.5
1.2 1 water
1.2 1 0.2M NaHCO₃ pH 9.5
Do not let slurry dry during washing.
6. Pour or scrape the Sepharose into 1-2 g protein/120 ml 0.2M NaHCO₃ pH 9.5 at 4° C.
7. Shake vigorously for 2 hours at 20° C.
8. Add 9 g glycine and shake additional ½ hour.
9. Wash in the scintered glass funnel with:
2 1 PBS
2 1 0.1M NaAc, 0.5M NaCl pH 4.0
800 ml column buffer Specific Example In the example presented here, hybridomas against HSA were made, one gram of mouse anti-HSA antibody was purified on a HSA-Sepharose column and these antibodies were coupled to Sepharose. Rat anti-mouse IgG hybridomas were raised and one was chosen to grow in culture and purify on the mouse IgG column. This rat-anti mouse IgG antibody was coupled to Sepharose and the affinity matrix was used to purify in a single step a mouse hybridoma directed against a guinea pig cell surface antigen.

Mouse anti-HSA hybridomas

On May 19, 1980, ten balb/c mice were immunized with HSA in the manner described in the protocol above. They were boosted on June 16, 1980 and on July 10, 1980, two mice were given an IV injection of 40 μg each of HSA in preparation for the cell fusion. The fusion procedure was carried out on July 17, 1980 by the methods detailed above. The fused cells were maintained in culture in the manner described above until July 28, 1980 when the first series of clones were tested for production of antibody against HSA (method described above). The second series of clones were tested on Aug. 7, 1980. Of the antibody producing clones that were detected, a total of nineteen were cloned and frozen for storage. One of these clones, designated OA10 was later chosen for expansion in large scale spinner culture for antibody production.

Preparation of the HSA-Sepharose column

In order to purify the anti-HSA antibody from the tissue culture supernatant, an inert matrix with HSA coupled to the surface was required. Accordingly ten grams of HSA were purchased from Sigma Chemical Co. and four grams were used in each of two runs to make HSA-Sepharose by the method of March et al. as described above. A total of 240 cc of HSA-Sepharose beads were made and these were packed in a 44×300 mm column (Amicon Corporation) in preparation for purifying the mouse anti HSA antibody from the tissue culture supernatants.

Production and Purification of Mouse IgG (Mouse anti HSA)

One of the mouse anti-HSA clones, designated OA10, produced in the run described above was chosen for large scale spinner culture for antibody production. This clone was generally gorwn in 10 or 20 liter batches in commercially available (Bellco Glass Co.) ten liter spinner flasks. The cells were grown in DMEM supplemented to 5% with normal calf serum. Antibiotics were also added. After the cells had grown and died (about one week) the culture supernatant was centrifuged to remove cell debris and the clear supernatant was passed through the 240 cc HSA-Sepharose column. The column was then washed overnight with approximately four liters of PBS and the mouse antibody was removed from the column by running 0.1M glycine buffer (pH 2.5) through the column. After the protein peak had run off the column the glycine was neutralized with 0.25 volumes of 2M tris buffer (pH 8) and the antibody solution was stored at 4° C. for future use. Sodium azide was added to a final concentration of 0.02% as a perspective. The amounts of mouse antiHSA antibody recovered from the HSA Sepharose column in ten such runs are given below.

|   | Date | Mg of Antibody Recovered |
|---|---|---|
| 1 | 9/26/80 | 64 |
| 2 | 10/16/80 | 66 |
| 3 | 10/27/80 | 48 |
| 4 | 11/07/80 | 97 |
| 5 | 11/18/80 | 116 |
| 6 | 12/02/80 | 92 |
| 7 | 12/18/80 | 108 |
| 8 | 12/31/80 | 185 |
| 9 | 1/14/81 | 136 |
| 10 | 1/28/81 | 108 |

A total of 1020 mg were recovered in a volume of 828 ml giving a concentration of 1.23 mg/ml. Prior to coupling this antibody to Sepharose, a more concentrated protein solution was required. Accordingly, the antibody solution was concentrated to 4.5 mg/ml but in the process 22% of the antibody was lost secondary to denaturation and precipitation.

Preparation of the mouse IgG Sepharose

Seven hundred and ninety-eight mg of mouse antibody remained in 176 ml of buffer. This antibody was mixed with 60 cc of cyanogen bromide activated Sepharose 4B (method of March et al. as described above). It was found that 100 mg of antibody remained unbound to the Sepharose which gave a coupling efficiency of 87.5%. This gave 11.63 mg of mouse antibody bound per cc of Sepharose beads.

Preparation of the rat anti-mouse IgG hybridomas

On Apr. 25, 1980, seven Lewis rats were each immunized with 200/μg of Mouse IgG (purchased from Cappel Laboratories) in the manner described above. They were boosted on May 29, June 20, July 29, August 22, and on Sept. 11, 1980; two rats were given an I.V. injection of 200 μg of mouse IgG in preparation for the cell fusion procedure. On Sept. 15, 1980, the spleens of the two rats were removed, prepared as a single cell suspension and processed for cell fusion and subsequent culture by the methods described above. A total of 320 clones were detected and tested for production of rat antibody which bound to mouse IgG. Only nine producing clones were found and of these, only one, designated AHF5, was found to be useful for antibody production. This cell line was grown in ten liter spinner cultures and the antibody was purified in the mouse IgG sepharose column.

Purification of the rat anti-mouse IgG antibody on the mouse IgG Sepharose column An initial batch of 20 liters of AHF5 culture supernatant was grown. In experiments in which small amounts of culture supernatant were passed over small amounts of the mouse IgG Sepharose beads, it was found that the rat anti mouse IgG antibody was present in the tissue culture supernatant at a concentration approximately 7 μg/ml and one cc of mouse IgG sepharose could bind 2.7 mg of rat anti-mouse IgG antibody. Since there were 11.63 mg of mouse IgG per ml of Sepharose bead, this means that 23% of the mouse IgG molecules on the beads were in an orientation which permitted the binding of the rat anti-mouse IgG antibody.

The 60 cc of Mouse IgG Sepharose was packed in a 22×300 mm Amicon column and approximately 14 liters of rat anti-mouse IgG culture supernatant was passed through the column. The column was washed with three liters of PBS and the rat anti-mouse IgG antibody was eluted from the column by passing 0.1M glycine buffer (pH 2.5) through the column. The protein peak was neutralized with 0.25 volumes of 2M tris buffer (pH 8.0). Eighty mg of rat antimouse IgG antibody were recovered in 50 cc.

In preparation for coupling the Sepharose, the antibody was concentrated by ammonium sulfate precipitation. An equal volume of 100% saturated ammonium sulfate solution was added to the antibody and the mixture was gently stirred for one hour. The precipitate was centrifuged at 2000 RPM×25 minutes. The precipitate was redissolved in 8 ml of PBS and dialyzed against 0.2M $NaHCO_3$, pH 9.5 (2L×3). Ninety-one percent of the original antibody was recovered.

Preparation of the rat anti-mouse IgG Sepharose

Seventy-three mg of rat antibody in 16 ml of 0.2M bicarbonate buffer were mixed with 20 cc of cyanogen bromide activated Sepharose 4B-CL (method of March et al.). One and four tenths (1.4) mg of rat antibody did not bind to the activated Sepharose. Three and six tenths (3.6) mg of rat anti-mouse IgG antibody coupled per cc of Sepharose beads.

Purification by affinity chromatography of a hybridoma antibody which interacts with an as yet unidentified cell surface antigen As a component of an ongoing project, mouse hybridoma cell lines producing antibodies against a mixture of guinea pig cell surface antigens were produced and cloned by the methods outlined above. One of these clones, designated HA12, was choosen for antibody production in vitro. Approximately seven liters of culture supernatant were grown and after assessing the capacity of the rat anti-mouse IgG Sepharose column, the HA12 antibody was purified by affinity chromatography in one liter batches. The results of these runs are shown below.

Purification of HA12 mouse anti guinea pig cell surface antigen on a 20 cc rat anti mouse IgG Sepharose column

| Date | Amount loaded on column | Amount of Antibody Recovered after washing and glycine elution |
|---|---|---|
| 1. 4/14/81 | 1000 (cc) | 20.9 mg |
| 2. 4/15/81 | 1200 | 20.0 |
| 3. 4/16/81 | 800 | 18.3 |
| 4. 4/17/81 | 900 | 17.8 |
| 5. 4/21/81 | 980 | 17.2 |
| 6. 4/22/81 | 940 | 18.2 |
| 7. 4/28/81 | 680 | 13.0 |

The column used to purify the HA12 antibody is the same one prepared in the previous section. Thus 71.6 mg of rat antimouse IgG antibody were present on 20 cc of Sepharose beads. The total column capacity was 20.9 mg of mouse antibody. Thus 29% of the rat antibody molecules on the Sepharose, were oriented such that they were capable of binding a mouse antibody.

From the foregoing it should be clear that the broad concept of the invention is to utilize an inexpensive protein to produce a general affinity reagent for the purification of a protein that occurs in very dilute solution. The foregoing example is directed to the ultimate production of a mouse monoclonal antibody utilizing human serum albumin as the inexpensive starting reagent. It should be appreciated, however, that the invention is applicable to the production of any protein which is produced in dilute solutions and the inexpensive starting material can be any protein which is capable of ultimately binding the protein sought for refinement.

The invention may be embodied in other specific forms without departing from the spirit or essential characteristics thereof. The present embodiments are therefore to be considered in all respects as illustrative and not restrictive, the scope of the invention being indicated by the appended claims rather than by the foregoing description, and all changes which come within the meaning and range of equivalency of the claims are therefore intended to be embraced therein.

I claim:

1. A process for purifying species specific antibodies by affinity chromatography comprising:
   A. producing a first antibody secreted by a hybridoma grown in vitro capable of binding to an antigen;
   B. providing a first column having immobilized thereon an antigen capable of binding the hybridoma secreted antibody produced in step A;
   C. binding the hybridoma secreted antibody of step A to the antigen on the column of step B;
   D. separating the first hybridoma secreted antibody from the antigen on the column of step C;
   E. immobilizing the first hybridoma secreted antibody separated in step D on a second column;
   F. producing a second antibody secreted by a hybridoma grown in vitro capable of binding to the first hybridoma secreted antibody;
   G. binding the second hybridoma secreted antibody to the first hybridoma secreted antibody by passing the second hybridoma secreted antibody through the column of step E;
   H. separating the second hybridoma secreted antibody from the first hybridoma secreted antibody on the column of step G;
   I. immobilizing the second hybridoma secreted antibody separated in step H on a third column;
   J. binding antibody of a type and species to which the second hybridoma secreted antibody is specific by passing said antibody through the column of step I; and,
   K. separating the bound antibody from the second hybridoma secreted antibody on the column of step J to obtain the purified antibody.

2. The process as set forth in claim 1 wherein in step B the column that is provided has immobilized thereon albumin.

3. The process as set forth in claim 2 wherein the first hybridoma antibody produced in step A is a hybridoma produced mouse IgG.

4. The process as set forth in claim 3 wherein the second hybridoma secreted antibody produced in step F is a hybridoma produced rat anti-mouse IgG directed against the species specific region of the mouse IgG.

5. The process as set forth in claim 4 wherein in step J the antibody is mouse IgG.

6. The process as set forth in claim 2 wherein the second hybridoma secreted antibody produced in step F is a hybridoma produced rat anti-mouse IgG directed against the species specific region of the mouse IgG.

7. The process as set forth in claim 6 wherein in step J the antibody is mouse IgG.

8. The process as set forth in claim 1 wherein the second hybridoma secreted antibody produced in step F is a hybridoma produced rat anti-mouse IgG directed against the species specific region of the mouse IgG.

9. The process as set forth in claim 8 wherein in step J the antibody is mouse IgG.

10. The process as set forth in claim 1 wherein after the second hybridoma antibody is separated from the column of step G in step H, there is repetition of steps G and H until substantially more of the second hybridoma secreted antibody is obtained than the amount of the first hybridoma secreted antibody used to make the column of step E.

11. The process as set forth in claim 10 wherein after the mouse IgG is separated from the column of step J in step K, there is repetition of step J and K until more of the mouse IgG is obtained than the amount of the rat anti-mouse IgG used to make the column of step I.

12. The process as set forth in claim 1 wherein after the antibody to which the second hybridoma antibody is directed against is separated from the column of step J in step K, there is repetition of step J and K until more of said antibody is obtained than the amount of the second hybridoma secreted antibody used to make the column of step I.

13. A process for purifying mouse immunoglobulin by affinity chromatography comprising:

A. producing a mouse IgG from a hybridoma grown in vitro capable of binding to an antigen;
B. providing a first column having immobilized thereon the antigen to which the IgG produced in step A is directed against;
C. binding the mouse IgG of step A onto the antigen on the column of step B;
D. separating the mouse IgG from the antigen on the column of step C;
E. immobilizing the mouse IgG separated from step D onto a second column;
F. producing a rat anti-mouse IgG from a hybridoma grown in vitro;
G. binding the rat anti-mouse IgG to the mouse IgG by passing the rat anti-mouse IgG through the column of step E;
H. separating the rat anti-mouse IgG from the mouse IgG on the column of step G;
I. immobilizing the rat anti-mouse IgG separated in step H on a third column;
J. binding mouse IgG to the rat anti-mouse IgG by passing the mouse IgG through the column of step I; and,
K. separating the bound mouse IgG of step J from the column of step J to obtain purified mouse IgG.

14. The process as set forth in claim 13 wherein after the rat anti-mouse IgG is separated from the column of step C in step H, there is repetition of steps G and H until substantially more of the rat anti-mouse IgG is obtained than the amount of the mouse IgG used to make the column of step E.

15. The process as set forth in claim 14 wherein after the mouse IgG is separated from the column of step J in step K, there is repetition of steps J and K until substantially more of the mouse IgG is obtained than the amount of rat antimouse IgG used to make the column of step I.

16. The process as set forth in claim 13 wherein after the mouse IgG is separated from the column of step J in step K, there is repetition of steps J and K until substantially more of the mouse IgG is obtained than the amount of rat anti-mouse IgG used to make the column of step I.

* * * * *